US012558000B2

(12) United States Patent
Presura et al.

(10) Patent No.: US 12,558,000 B2
(45) Date of Patent: Feb. 24, 2026

(54) ESTIMATING THE THICKNESS OF RIGID MATERIAL IN A TOOTH

(71) Applicant: KONINKLIJKE PHILIPS N.V., Eindhoven (NL)

(72) Inventors: Cristian Nicolae Presura, Veldhoven (NL); Jindřich Charvat, Statenice (CZ); Martin Pekar, Eindhoven (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 200 days.

(21) Appl. No.: 18/268,024

(22) PCT Filed: Dec. 15, 2021

(86) PCT No.: PCT/EP2021/085837
§ 371 (c)(1),
(2) Date: Jun. 16, 2023

(87) PCT Pub. No.: WO2022/129134
PCT Pub. Date: Jun. 23, 2022

(65) Prior Publication Data
US 2024/0065578 A1 Feb. 29, 2024

(30) Foreign Application Priority Data

Dec. 16, 2020 (EP) ..................................... 20214511
Sep. 23, 2021 (EP) ..................................... 21198556

(51) Int. Cl.
*A61B 5/107* (2006.01)
*A61B 5/00* (2006.01)

(52) U.S. Cl.
CPC .......... *A61B 5/1075* (2013.01); *A61B 5/0088* (2013.01); *A61B 2560/0431* (2013.01)

(58) Field of Classification Search
CPC ................ A61B 5/1075; A61B 5/0088; A61B 2560/0431; A61B 5/6844; A61B 5/682; A61B 5/0075; A61C 1/082; A61C 19/04
See application file for complete search history.

(56) References Cited

U.S. PATENT DOCUMENTS 5,725,480 A * 3/1998 Oosta ..................... A61B 5/442
600/556
5,818,587 A 10/1998 Devaraj et al.
(Continued)

FOREIGN PATENT DOCUMENTS

CN 110559091 A 12/2019
JP 2013233303 A 11/2013
(Continued)

OTHER PUBLICATIONS

International Search Report and Written Opinion Dated Mar. 7, 2022 For International Application No. PCT/EP2021/085837 Filed Dec. 15, 2021.
(Continued)

*Primary Examiner* — Baisakhi Roy

(57) ABSTRACT

A device for estimating the thickness of rigid material in a tooth covering the pulp of the tooth. The device comprises a light source arrangement configured to emit light at a first wavelength and light at a second wavelength onto the tooth and a sensor arrangement for measuring the intensity of light reflected and scattered from the tooth corresponding to the first and second wavelengths. The device also comprises a processor configured to receive a first intensity map corresponding to the first wavelength and a second intensity map corresponding to the second wavelength from the sensor arrangement, analyze the first intensity map and the second intensity map to asses the amount of light reflected and scattered from the tooth corresponding to the first wave-
(Continued)

length and the second wavelength and estimate an indication of thickness for the rigid material covering the pulp of the tooth based on the analysis.

14 Claims, 5 Drawing Sheets

(56)                    References Cited

U.S. PATENT DOCUMENTS

| | | | | |
|---|---|---|---|---|
| 6,957,099 | B1 * | 10/2005 | Arnone | G01N 21/3586 |
| | | | | 600/473 |
| 2001/0049082 | A1 * | 12/2001 | Kerschbaumer | A61C 19/10 |
| | | | | 356/408 |
| 2005/0100866 | A1 * | 5/2005 | Arnone | A61B 5/417 |
| | | | | 433/29 |
| 2007/0021670 | A1 * | 1/2007 | Mandelis | A61B 5/0088 |
| | | | | 600/473 |
| 2008/0024788 | A1 * | 1/2008 | Shimizu | G01B 9/02091 |
| | | | | 356/497 |
| 2009/0087811 | A1 * | 4/2009 | Ertl | A61B 5/0088 |
| | | | | 433/29 |
| 2009/0155735 | A1 | 6/2009 | Hauger | |
| 2010/0172842 | A1 * | 7/2010 | Israeli | A61N 2/006 |
| | | | | 600/420 |
| 2010/0253773 | A1 | 10/2010 | Oota et al. | |
| 2011/0102566 | A1 * | 5/2011 | Zakian | A61B 5/0086 |
| | | | | 348/66 |
| 2012/0200687 | A1 * | 8/2012 | Kikuchi | A61B 1/0653 |
| | | | | 348/370 |
| 2014/0293289 | A1 * | 10/2014 | Reisman | G01B 9/02091 |
| | | | | 356/479 |
| 2019/0269485 | A1 * | 9/2019 | Elbaz | A61B 5/1079 |
| 2020/0015923 | A1 | 1/2020 | Scheib et al. | |
| 2022/0400964 | A1 * | 12/2022 | Imai | G01N 21/27 |

FOREIGN PATENT DOCUMENTS

| | | | |
|---|---|---|---|
| WO | 2007072592 | A1 | 6/2007 |
| WO | 2014105521 | A1 | 7/2014 |
| WO | 2017045773 | A1 | 3/2017 |

OTHER PUBLICATIONS http://www.confidentabc.com/ Real time feedback with ConfiDent - Specially designed for the accurate placement of dental implants. copyright 2021 @ ConfiDent ABC.

Bjorndal et al.; "Management of deep caries and the exposed pulp" First published: Apr. 15, 2019 International Endodontic Journal, 52, 949-973, 2019. https://doi.org/10.1111/iej. 13128 https://onlinelibrary.wiley.com/doi/pdfdirect/10.1111/iej. 13128.

Bakland, Leif K .; "Dental trauma guidelines"; Pediatric Dentistry, 2013; 35(2), 106-108.

Bhaskar et al.; "Dental vitality tests and pulp status"; Journal of the American Dental Association, vol. 86 (2), Feb. 1973; 409-411. https://doi.org/10.14219/jada.archive. 1973.0081.

Bi et al.; "Verification of accuracy of an algorithmic image-based dental pulp vitality test"; Medical Imaging 2020: Computer-Aided Diagnosis, edited by H. K. Hahn & M. A. Mazurowski (Eds.), Proc. of SPIE vol. 11314, p. 145. https://doi.org/10.1117/12.2549744.

Gopikrishna, V et al.; (2009). "Assessment of pulp vitality: a review" International Journal of Paediatric Dentistry, 19 (1), 3-15. https://doi.org/10.1111/j. 1365-263X.2008.00955.x.

Holland, G. R .; "Morphological features of dentine and pulp related to dentine sensitivity"; Archives of Oral Biology, vol. 39, Supplement, 1994, pages S3-S11. https://doi.org/10.1016/0003-9969(94)90182-1.

Karayilmaz, H et al.; "Comparison of the reliability of laser Doppler flowmetry, pulse oximetry and electric pulp tester in assessing the pulp vitality of human teeth"; (2011) Journal of Oral Rehabilitation, 38(5), 340-347. https://doi.org/10.1111/j. 1365-2842.2010.02160.x.

Kwon, et al.; "Thermal irritation of teeth during dental treatment procedures"; (2013), Restorative Dentistry & Endodontics, 38(3), 105. https://doi.org/10.5395/rde.2013.38.3.105.

Lejeune et al.; "A review of odontogenic infections"; In The Journal of the Louisiana State Medical Society: official organ of the Louisiana State Medical Society; (1994), (vol. 146, Issue 6, pp. 239-241). https://pubmed.ncbi.nlm.nih.gov/8057047/.

Matsutani et al.; "Stimulation of the locus coeruleus suppresses trigeminal sensorimotor function in the rat"; Brain Research Bulletin, vol. 53 Issue 6, pp. 827-832, 2000. https://doi.org/10.1016/S0361-9230(00)00426-3.

Mendes et al.; "Evaluation of magnetic resonance imaging for diagnostic purposes in operative dentistry-a systematic review"; Clinical Oral Investigations (vol. 24, Issue 2, pp. 547-557); 2020. Springer. https://doi.org/10.1007/s00784-019-03103-8.

Nagaoka et al.; "Bacterial invasion into dentinal tubules of human vital and nonvital teeth"; Journal of Endodontics, 21 (2), 70-73. 1995. https://doi.org/10.1016/S0099-2399(06)81098-8.

Paphangkorakit et al.; "Discrimination of hardness by human teeth apparently not involving periodontal receptors"; Archives of Oral Biology, vol. 43, Issue 1, Jan. 18, 1998, pp. 1-7. https://doi.org/10.1016/S0003-9969(97)00090-3.

Tymofiyeva et al.; "High-resolution 3D magnetic resonance imaging and quantification of carious lesions and dental pulp in vivo"; Magnetic Resonance Materials in Physics, Biology and Medicine, 2009, 22(6), 365-374. https://doi.org/10.1007/s10334-009-0188-9.

Walsh, L.J .; "Serious complications of endodontic infections: Some cautionary tales" Australian Dental Journal, (1997) 42(3), 156-159. https://doi.org/10.1111/j. 1834-7819.1997.tb00113.x.

Yu, C et al.; "An overview of the dental pulp: its functions and responses to injury"; Australian Dental Journal, 2007; 52 (1 Suppl), S4-S6. https://doi.org/10.1111/j. 1834-7819.2007.tb00525.x.

"Pathways of the Pulp" 6 th Edition. Edited by: COHEN, Stephen and BURNS, Richard C. Henry O. Trowbridge, & Kim, S. (n.d.). "Pulp development, structure and function." (Chapter 11) (In: Cohen S, Burns RC, eds. Pathways of the Pulp. St. Louis: Mosby (1998th ed.). 1998. Retrieved Jul. 18, 2020, from https://www.academia.edu/16279447/Cohens_Pathways_of_the_Pulp_10th_ed ._ dentistry _-_ K ._ Hargreaves_et ._ al.

* cited by examiner

ESTIMATING THE THICKNESS OF RIGID MATERIAL IN A TOOTH

This application is the U.S. National Phase application under 35 U.S.C. § 371 of International Application No. PCT/EP2021/085837, filed on Dec. 15, 2021, which claims the benefit of EP application Nos. 20214511.6, filed Dec. 16, 2020 and 21198556.9, filed Sep. 23, 2021. These applications are hereby incorporated by reference herein.

FIELD OF THE INVENTION

The present invention relates to the field of oral treatment, and more particularly to concepts for estimating the thickness of rigid material in a tooth covering the pulp of the tooth.

BACKGROUND OF THE INVENTION

The dental pulp resides in a rigid chamber comprising dentine, enamel and cementum, which provide strong mechanical support and protection from the microbial-rich oral environment. However, if this rigid shell loses its integrity due to caries, cracks or other openings, it gets inflamed and eventually necrotic. If untreated, periapical pathosis may occur.

Dental pulp fulfills the following essential functions such as increasing the resistivity of the tooth to bacterial invasion, provide warning mechanisms due to its sensitivity to thermal and mechanical stimuli and provide a force feedback loop to masticatory muscles.

The integrity of the dental pulp can be damaged by tooth decay, removal of the tooth decay by dental drill, heat irritation during various dental procedures when the dentine thickness is less than 1 mm (e.g. preparations, light curing, etc.) or tooth injury (e.g. luxation, crown fracture, etc.). The ability to measure distance to the pulp in the range from about 2 mm to 0.2 mm is essential in order to avoid any of the above listed adverse events or to choose the right treatment method.

Standard caries treatment may take as little as about 10 minutes. However, this simple treatment can turn into a time-consuming and expensive root canal treatment in the cases where the pulp gets unintendedly exposed. The most simple root canal treatment takes at least one and a half hours. Unintended pulp exposure occurs in 29% of deep caries excavations.

The problem to solve is how to detect presence and distance to the dental pulp in an unobtrusive manner. Preferable, the solution does not affect the state-of-the-art work-flow of excavation. This is difficult to do in common dental practice as the dentist has to rely solely on their experience, knowledge of the tooth anatomy, visual appearance and, sometimes, on X-ray imaging. However, X-ray imaging provides only limited views, increases the treatment time, and utilizes harmful ionizing radiation.

Although the failure rate of the unintended pulp exposure can be reduced to 18% by utilizing stepwise excavation, it comes at the cost of increased risk of pulp exposure during the removal of temporary filling or final excavation, additional discomfort to the patient, and increased cost. Moreover, the chance that patients will not return to the dentist to conclude a multiple-appointment treatment can lead to treatment failure. Thus, there is a clear need of a way of avoiding unintended pulp exposure.

SUMMARY OF THE INVENTION

The invention is defined by the claims.

According to examples in accordance with an aspect of the invention, there is provided a device for estimating the thickness of rigid material in a tooth covering the pulp of the tooth, the device comprising:

a light source arrangement configured to emit light at a first wavelength and light at a second wavelength onto the tooth;

a sensor arrangement for measuring the intensity of light reflected and scattered from the tooth corresponding to the first and second wavelengths; and a processor configured to:

receive a first intensity map from the sensor arrangement corresponding to the first wavelength;

receive a second intensity map from the sensor arrangement corresponding to the second wavelength;

analyze the first intensity map and the second intensity map to asses the amount of light reflected and scattered from the tooth corresponding to the first wavelength and the second wavelength; and estimate an indication of thickness for the rigid material covering the pulp of the tooth based on the analysis.

The inventors realized that, for some thicknesses, the rigid material of a tooth (i e enamel and dentine) allows some light through to the dental pulp. They also realized that the blood in the dental pulp can then absorb or reflect the light. In some cases, the absorption and/or reflection is dependent on the wavelength of the light. The amount of light reflected by the blood in the dental pulp can be measured from the surface of the tooth and will depend on the thickness of the rigid material through which the reflected light has to travel.

It is thus proposed to emit light at two wavelengths onto the tooth and measure the intensity of the light reflected and scattered by the tooth. For example, two LEDs could be used to illuminate the tooth with light of two wavelengths. Alternatively, a white light may be used with two light filters which only allow one particular wavelength.

The intensity maps for both wavelengths may be measured at different times or at the same time. For example, the sensor arrangement may have two cameras with filters in order to obtain the intensity maps for the two wavelengths at the same time. Alternatively, a first LED corresponding to the first wavelength may be actuated first and the first intensity map obtained and, subsequently, the second LED corresponding to the second wavelength is actuated and the second intensity map obtained.

An intensity map corresponds to a 2D measurement of the intensity of light at a corresponding wavelength for an area of the tooth. For example, the sensor arrangement may be configured to measure the intensity of the reflected and scattered light from the tooth at two wavelengths and construct two intensity maps which reflect the intensity of light at the first wavelength and the second wavelength respectively for an area of the tooth.

The intensity values of the intensity maps will differ depending on the corresponding wavelength and also based on the thickness of the rigid material. For example, for thin thicknesses (e.g. below 1 mm) of rigid material, the light emitted will likely interact with the pulp and thus the reflected and scattered light at that position of the intensity map will be different than other areas of the tooth with thicker rigid material (e.g. >2 mm). The relationship between wavelengths and intensity values at different wavelengths can be found experimentally. Thus, by analyzing the first intensity map and the second intensity map, an indication of thickness for the rigid material can be found.

Various methods for analyzing the first and second intensity values will be further explained below.

The intensity maps may comprise a plurality of intensity values corresponding to different areas of the tooth. Each intensity value may be a measurement of the intensity of light the corresponding wavelength.

The indication of thickness may provide an estimated thickness value or an indication of when, for example, the thickness is likely to be above or below a particular threshold (e.g. >2 mm, <0.2 mm or between 2 mm and 0.2 mm). The possible indications of thickness may depend on the first wavelength and the second wavelength used. Alternatively, the indication of thickness could provide a "thickness map" which gives an estimate of thickness for different areas of the tooth.

The light source arrangement may comprise a single light emitting element capable of emitting light of at least two wavelengths. Alternatively, the light source arrangement may comprise two light emitting elements each for emitting light at the first and second wavelengths respectively. The light source arrangement may emit light at a plurality of wavelengths (e.g. white light) and the sensor arrangement may be configured to measure light of at least two of the plurality of wavelengths.

The sensor arrangement may comprise one or more cameras and the intensity maps received may correspond to images obtained by the cameras. For example, a single camera may be used which can capture light reflected at any wavelength in the visible spectrum. Alternatively, the sensor arrangement may comprise one or more sensing elements which can measure light of particular wavelengths (or a range of particular wavelengths).

The device may be calibrated by identifying a direction through a tooth which does not traverse through blood or dental pulp in the tooth, emitting light at a first wavelength in the identified direction (thus obtaining a first calibrated intensity value corresponding to the first wavelength) and emitting light at a second wavelength in the identified direction (thus obtaining a second calibrated intensity value corresponding to the second wavelength).

Blood may have a higher absorptivity for light at the first wavelength than light at the second wavelength.

By emitting light at two wavelengths, one of which is absorbed by the blood more than the other, it is possible to further estimate the thickness of the rigid material and thus estimate the presence of, and distance to, the pulp.

The intensity value of the first intensity map corresponding to the first wavelength (i.e. absorbed by blood) will show any area of the tooth where the rigid material is relatively thin (typically <<1 mm) as having a relatively low intensity. However, there may be other "low light areas" of the rigid material which have a low intensity for the first wavelength for other reasons.

The intensity values of the second intensity map corresponding to the second wavelength (i.e. reflected by blood) will not have such a low intensity at areas where the rigid material is relatively thin but will likely have a low intensity in the other "low light areas".

Thus, a comparison/analysis between the first intensity value and the second intensity value could indicate where the rigid material is thin and provide an indication of the thickness.

The processor may be configured to analyze the first intensity map and the second intensity map by determining the difference and/or a ratio between corresponding intensity values of the first intensity map and the second intensity map.

The difference between corresponding intensity values of the two intensity maps can be used to determine the thickness of the rigid material. A relationship between rigid material thickness and the differential intensity (between first and second intensity value) could be found experimentally, for example. The relationship will depend on the choice of first wavelength and second wavelength.

Additionally, when plotted in a spectral plot (i.e. intensity against wavelength), the gradient between the intensity values corresponding to the first and second wavelengths can be further utilized in the analysis to estimate the indication of thickness for the rigid material (and thus proximity to the dental pulp).

The processor may be further configured to analyze the first intensity map and the second intensity map by determining the integrals of intensity with respect to wavelength between the first wavelength and the second wavelength based on corresponding intensity values of the first intensity map and the second intensity map.

The inventors have found a relationship between the thickness of the rigid material and the integral of intensity with respect to wavelength (between two wavelength values). Thus, the intensity values of the first and second intensity maps can further aid in estimating the thickness of the rigid material when it is thinner than, for example, 2 mm (dependent on the wavelengths used).

The first wavelength may be between 500 nm and 600 nm and preferably between 530 nm and 550 nm or between 570 nm and 590 nm.

When the rigid material has a thickness of more than around 0.5-2 mm, the absorption of blood in the dental pulp is prominent for some wavelengths of green light. These peaks are caused by the hemoglobin (oxygenated, deoxygenated etc.) in blood. This can be seen, for example, by two peaks (around 540 nm and 580 nm) in a spectral map. The thicker the rigid material is, the less prominent the peaks will be (i.e. as if there was no blood behind the rigid material). Thus, the difference between reflected light intensity values at two wavelengths (one which is green and thus more absorbed by blood than the other) can give an indication of the thickness of the rigid material for thicknesses below 2.5 mm and above around 0.5 mm. For thicknesses below around 0.5 mm, the blood will likely absorb most of the light and thus there may be no peaks.

The second wavelength may be between 600 nm and 800 nm.

The device may further comprise a cross-polarizer, wherein the cross-polarizer comprises a first polarizing element placed in front of the light source arrangement and a second polarizing element in front of the sensor arrangement and wherein the first polarizing element is orthogonal to the second polarizing element.

The cross-polarizer may reduce specular reflections by using orthogonal light polarization between the light from the light source and the reflected light measured at the light sensor, thus increasing contrast in the acquired intensity signals.

The light source arrangement may be further configured to emit light at a third wavelength, wherein blood has a higher absorptivity for light at the third wavelength than light at the second wavelength and blood has a lower absorptivity for light at the third wavelength than light at the first wavelength. The processor may be further configured to receive a third intensity map from the sensor arrangement corresponding to the third wavelength and analyze the third intensity map to assess the amount of light reflected and scattered from the tooth corresponding to the third wavelength.

For example, the first wavelength may be chosen such that blood has a high absorptivity (e.g. 540 nm) for it, the second wavelength may be chosen such blood has a low absorptivity (e.g. 650 nm) for it and the third wavelength may be chosen such that blood has a high absorptivity (560 nnm) for it, but not as high as for the first wavelength.

The relationship between light wavelength and absorptivity is known for the main components of blood (i.e. oxygenated hemoglobin, deoxygenated hemoglobin etc.) and thus the relationships between the first and third (or the second and third) can be further used to estimate the thickness of the rigid material.

The light source arrangement may comprise one or more light guides and one or more light emitting elements connected to a proximal end of the light guides.

By using light guides (e.g. fiber optic cable), the section of the light source arrangement which emits the light can be made smaller. For example, the light emitting elements (e.g. light emitting diodes LEDs) can be placed at a section of the device proximal to a user and the proximal end of the light guides can be connected to the light emitting elements. The distal end (light emitting end) can then be placed at a distal end of the device which is to be placed near the tooth.

The invention also provides a handheld dental probe comprising:

a housing comprising:
    an illumination window at a distal end of the housing;
    and
    a rotor; and
    the device for estimating the thickness of rigid material in a tooth covering the pulp of the tooth, wherein the light source arrangement and the sensor arrangement are facing the illumination window.

The housing of the handheld device may further comprise a fluid path for allowing fluids to flow to the distal end of the housing and one or more fluid outlets at a distal end of the housing. The handheld dental device may further comprise a drill connected to a distal end of the rotor.

The invention also provides a method for estimating the thickness of rigid material in a tooth covering the pulp of the tooth, the method comprising:

receiving a first intensity map from a sensor arrangement corresponding to a first wavelength, wherein the first intensity map comprises data of the intensity of light of the first wavelength reflected and scattered from the tooth;

receiving a second intensity map from the sensor arrangement corresponding to a second wavelength, wherein the second intensity map comprises data of the intensity of light of the second wavelength reflected and scattered from the tooth;

analyzing the first intensity map and the second intensity map to asses the amount of light reflected and scattered from the tooth corresponding to the first wavelength and the second wavelength; and estimating an indication of thickness for the rigid material covering the pulp of the tooth based on the analysis.

Blood may have a higher absorptivity for light at the first wavelength than light at the second wavelength.

Analyzing the first intensity map and the second intensity map may comprise determining the difference and/or a ratio between corresponding intensity values of the first intensity map and the second intensity map.

Analyzing the first intensity map and the second intensity map may comprise determining the integrals of intensity with respect to wavelength between the first wavelength and the second wavelength based on corresponding intensity values of the first intensity map and the second intensity map.

The invention also provides a computer program product comprising computer program code which, when executed on a computing device having a processing system, cause the processing system to perform all of the steps of the method for estimating the thickness of rigid material in a tooth covering the pulp of the tooth.

These and other aspects of the invention will be apparent from and elucidated with reference to the embodiment(s) described hereinafter.

BRIEF DESCRIPTION OF THE DRAWINGS

For a better understanding of the invention, and to show more clearly how it may be carried into effect, reference will now be made, by way of example only, to the accompanying drawings, in which: dentine.

DETAILED DESCRIPTION OF THE EMBODIMENTS

Figure 1:
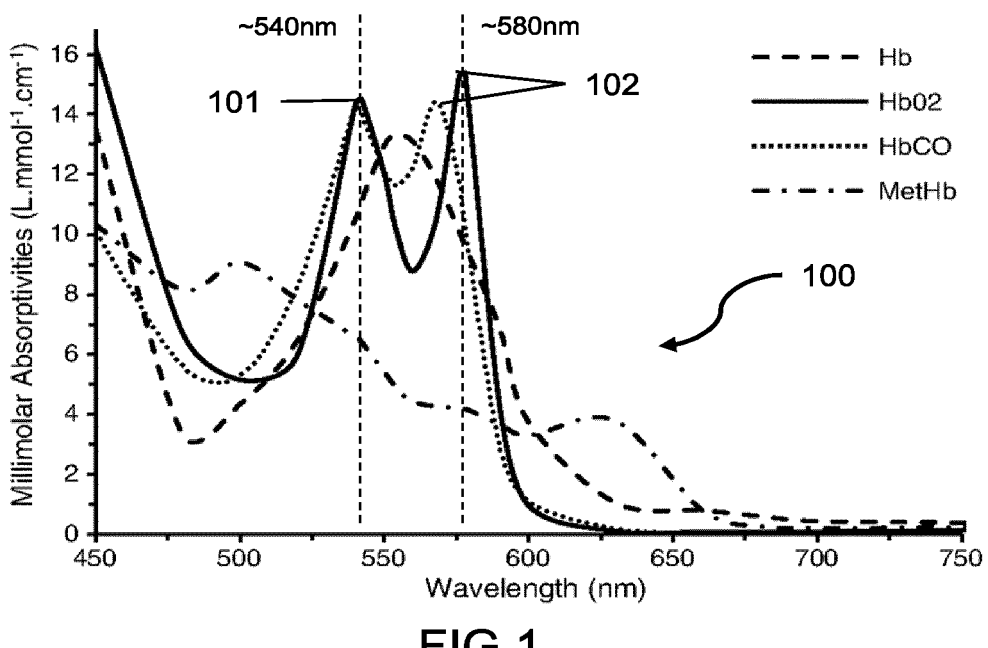
FIG. 1 shows absorption spectra of blood.

The invention will be described with reference to the Figures.

It should be understood that the detailed description and specific examples, while indicating exemplary embodiments of the apparatus, systems and methods, are intended for purposes of illustration only and are not intended to limit the scope of the invention. These and other features, aspects, and advantages of the apparatus, systems and methods of the present invention will become better understood from the following description, appended claims, and accompanying drawings. It should be understood that the Figures are merely schematic and are not drawn to scale. It should also be understood that the same reference numerals are used throughout the Figures to indicate the same or similar parts.

The invention provides a device for estimating the thickness of rigid material in a tooth covering the pulp of the tooth. The device comprises a light source arrangement configured to emit light at a first wavelength and light at a second wavelength onto the tooth and a sensor arrangement for measuring the intensity of light reflected and scattered from the tooth corresponding to the first and second wavelengths. The device also comprises a processor configured to receive a first intensity map corresponding to the first wavelength and a second intensity map corresponding to the second wavelength from the sensor arrangement, analyze the first intensity map and the second intensity map to asses the amount of light reflected and scattered from the tooth corresponding to the first wavelength and the second wavelength and estimate an indication of thickness for the rigid material covering the pulp of the tooth based on the analysis. Experimental Discovery:

FIG. 1 shows absorption spectra of blood 100, wherein the horizontal axis displays wavelength (nm) and the vertical axis displays millimolar absorptivity (L·mmol-1·cm-1). Hemoglobin (Hb), oxyhemoglobin (HbO2) and carboxyhemoglobin (HbCO) have peaks at different wavelengths in the vicinity of 500 nm to 600 nm. Thus, the overall absorption spectra of blood will depend on the particular ratios of hemoglobin. Methemoglobin (MetHb) does not have similar peaks to the other types of hemoglobin, however, it is usually found in small concentrations (1-2% in healthy subjects) and thus may not affect the spectra significantly.

Further investigations have shown that the absorption spectra of blood may display two absorption peaks: one at roughly 540 nm and a second at roughly 580 nm, such that the peaks often fall within the range 520-550 nm and 570-590 nm. As observed in FIG. 1, the peak 101 occurs at a wavelength of ~540 nm and the peaks 102 occur either side of a wavelength of ~580 nm.

Figure 2:
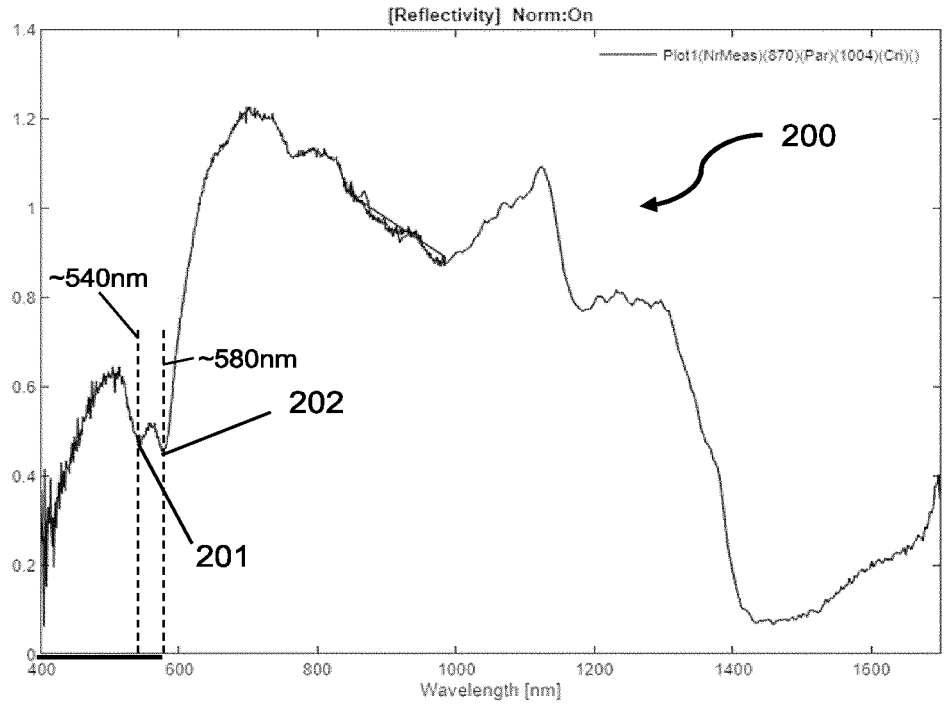
FIG. 2 shows a measured reflectivity spectrum for the case of a 1 mm thick slice of dentine.

The reflectivity spectra of visible light reflected and scattered by the tooth has also been investigated and reflectivity spectrums are shown in FIGS. 2 and 3.

The proposed measurement technique for experimentation makes use of optical spectroscopy in which a broadband light source is used to illuminate the tooth through fiber optics. The reflected light is collected and guided by another (or the same) fiber after being scattered and absorbed in the tooth. One of the different approaches of translating the obtained spectral information into clinically relevant parameters is the direct correlation of the measured spectra with known tissue type. These methods generally do not require prior knowledge of complex interaction of light tissues.

FIG. 2 shows a reflectivity spectrum 200 for the case of a 1 mm thick slice of dentine covering the pulp of the tooth, wherein the horizontal axis displays wavelength (nm) and the vertical axis displays the normalized reflectivity (arbitrary units). Troughs in reflectivity can be observed in FIG. 2: the trough 201 occurs at ~540 nm and a second trough 202 occurs at ~580 nm. The absorption peaks 101, 102 in FIG. 1 occur at very similar wavelengths to the reflectivity troughs 201, 202, and reflectivity is also decreased in the range 400 nm to 600 nm, which coincides with the increased absorption shown in FIG. 1 in the range 450 nm to 600 nm. Thus, it may be inferred that the visible light is absorbed by the blood of the pulp. Therefore, the absorption spectrum of the blood contained in the pulp of the tooth can be related to the reflectivity spectra of visible light reflected/scattered by the dentine of the tooth, such that absorption peaks correspond to reflectivity troughs.

Investigations have also shown that dentine thicknesses thinner than 2 mm can exhibit decreased absorption and hence increased reflectivity in the range 400 nm to 600 nm, and that the variables may be dependent.

Figure 3A:
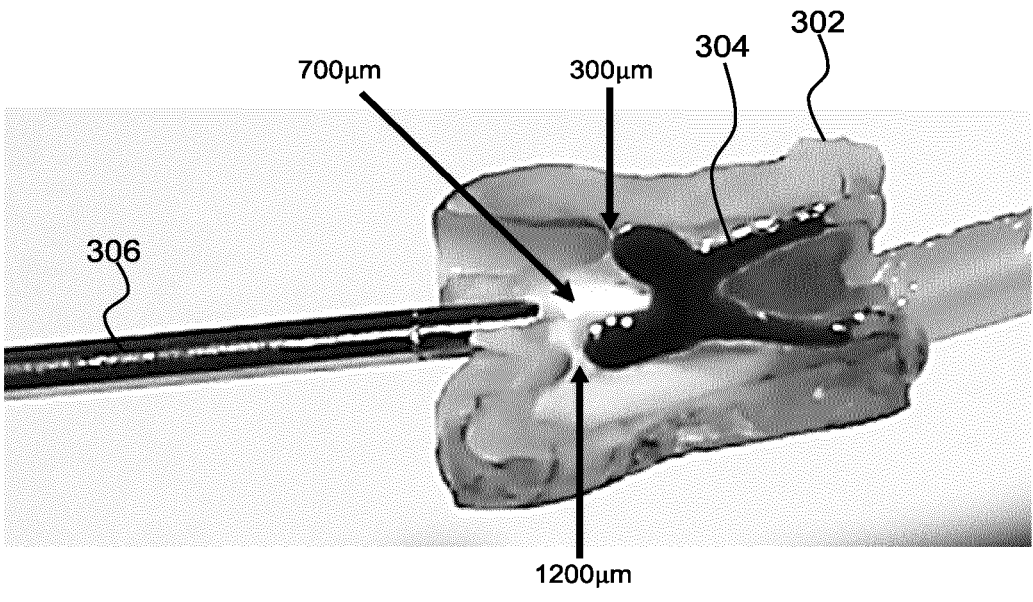
FIG. 3A shows an experimental setup used to obtain the optical footprint of dental pulp filled with blood behind various thicknesses of dentine.
Figure 3B:
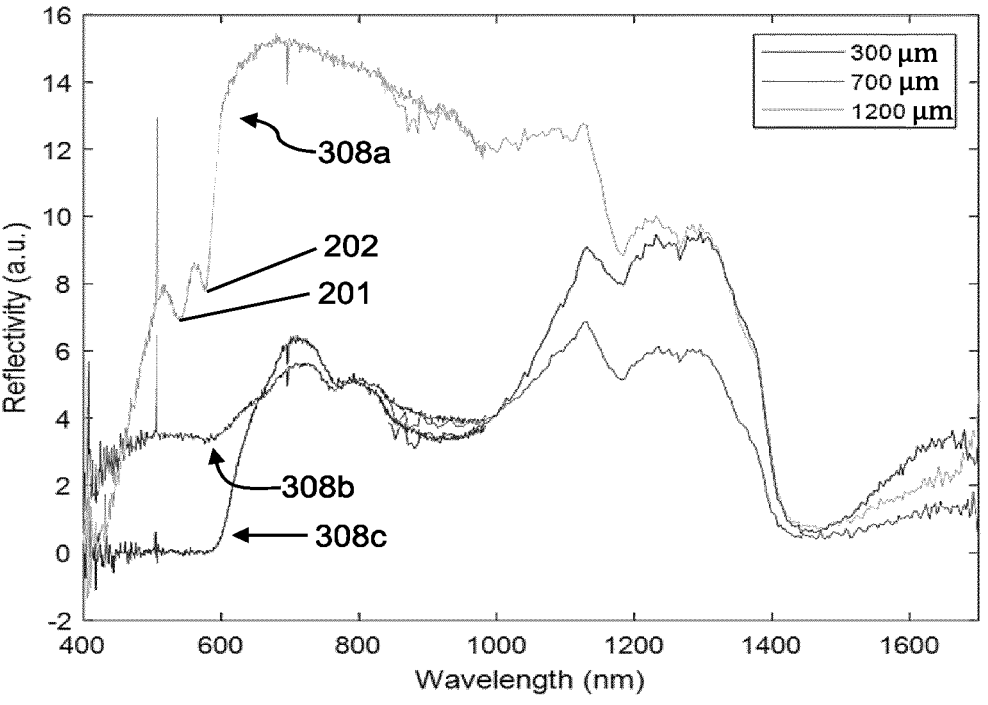
FIG. 3B shows the measured reflectivity spectra for three thicknesses obtained with the experimental setup of FIG. 3A.

FIG. 3A shows an experimental setup used to obtain the optical footprint of dental pulp 304 filled with blood behind various thicknesses of dentine and FIG. 3B shows the corresponding measured reflectivity spectra 308a, 308b and 308c (arbitrary units for reflectivity) for three thicknesses (0.3 mm, 0.7 mm and 1.2 mm).

Three holes were drilled in the tooth 302 to various distances to the pulp 304. The tooth 302 was cut in half and the pulp 304 was filled with blood. FIG. 3A is a photograph of the experimental setup. The probe 306 was used to obtain the reflectivity spectra 308a, 308b and 308c for each of the three holes The first spectrum 308a (with corresponding distance to the pulp 304 of 1200 um) shows two dips 201 and 202 at around 540 nm and 580 nm respectively, which is a clear indication that light is absorbed by the blood. However, the blood peaks diminish (and the overall reflectivity is decreased) in the range from 400 nm until 600 nm as the probe 306 gets closer to the pulp 304. In fact, the reflectivity decreases for most wavelengths relative to the distance to the pulp 304 as can be seen by the second spectrum 308b (700 um) and the third spectrum 308c (300 um).

However, the afore-mentioned spectra measurements were performed using a probe 306 which needed to be placed against the tooth 302. In practice, this proximity to the tooth 302 would make it difficult to integrate into a drill or any other existing dental probes which have moving parts or don't have the necessary dimensions to fit into a hole in the tooth 302.

For example, when used in combination with a drill, the light source and the sensor (e.g. photodetector) would have to be placed at the distal end of the dental probe where the drill bit usually goes, but it is necessary to have the drill bit at the distal end in order to drill the tooth 302. Thus, a drill bit would have to be made which integrates the light source and the photodetector into the drill bit, adding complexity to the probe.
Methodology:

In order to make the device unobtrusive, it proposes to use a sensor to obtain intensity maps of the tooth for different wavelengths instead of obtaining a spectrum. Obtaining an intensity map does not require the sensor to be placed in contact with the tooth whilst enabling the reflected and scattered light to be measured.

Figure 4:
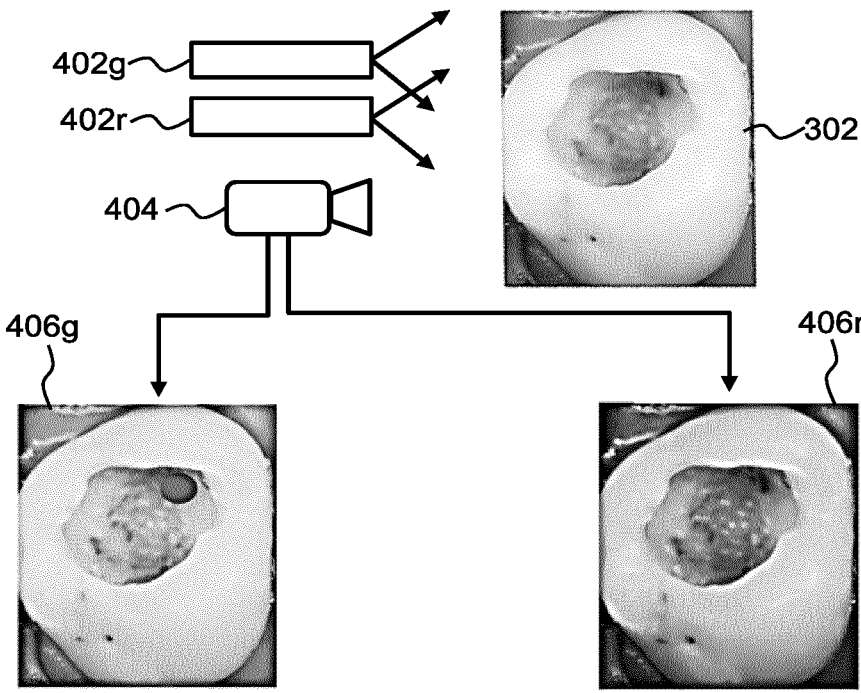
FIG. 4 shows a first embodiment according to the invention where double color illumination is used.

FIG. 4 shows a first embodiment according to the invention where double color illumination is used. The first embodiment uses a green light source 402g (e.g. a green LED) and a red-light source 402r (e.g. a red LED) to illuminate the tooth 302. A camera 404 is used to capture images (i.e. intensity maps) 406g and 406r of the tooth 302 after it has been illuminated. The brightness values for each pixel (or group of pixels) in an image correspond to the intensity values in an intensity map.

In a first use case of the first embodiment, the two light sources 402g and 402r are used alternately, illuminating the tooth 302 at different times. When the red illumination is used, the pulp will be hardly visible. This is because, for red light, blood has a low absorption level and thus the red light will be scattered in the pulp as in the dentine and the pulp will be hardly visible in contrast to the dentine (in the image 406r). When the green light is used, the pulp will be more visible as the green light will be more absorbed by the blood in the pulp and thus contrast more with the dentine (in the image 406g).

When the tooth 302 is illuminated with green light, the pulp will be more visible (i.e. contrast with respect to dentine will increase). This is because, for most green wavelengths, the absorption of light by the blood in the pulp is high (see FIG. 1). Less light will come back to the camera

404 from the region where the pulp is. In other words, the spot which reveals the pulp will be darker than the environment.

By using the two color images 406g and red 406r of the tooth 302, a contrast will appear in the location where the pulp is. This will reveal areas of the tooth 302 with a relatively thin layer of dentine covering the pulp.

Figure 5:
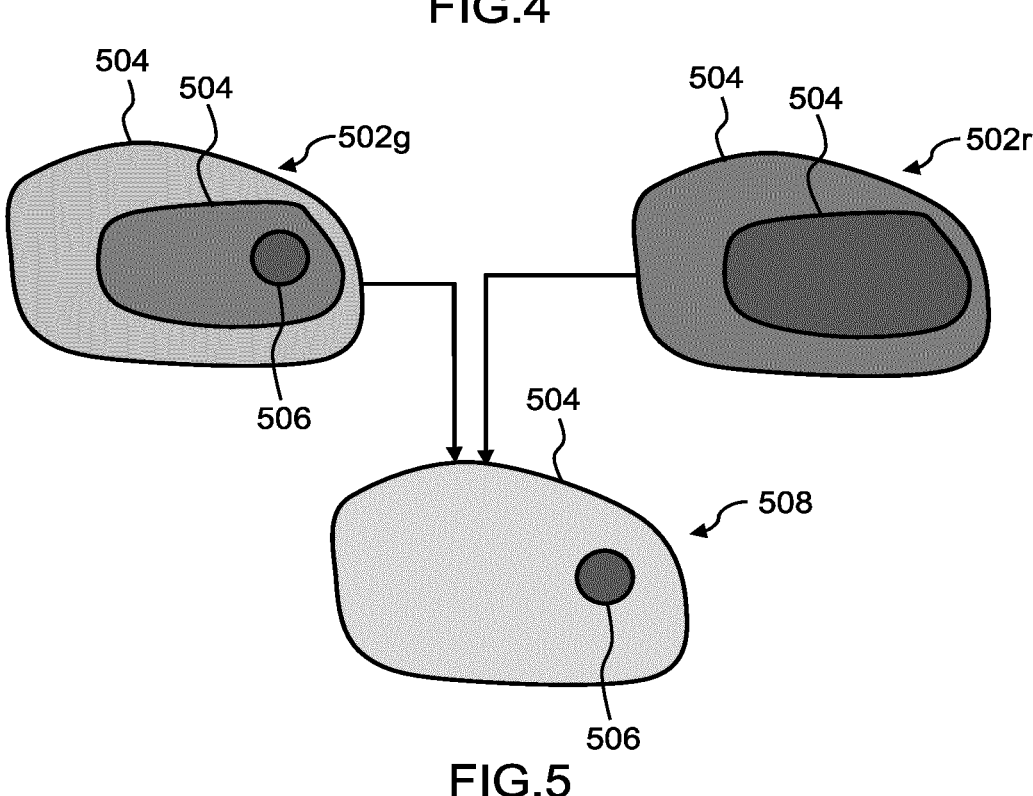
FIG. 5 shows an illustration of a method for analyzing the intensity maps of the tooth.

FIG. 5 shows an illustration of a method for analyzing the intensity maps 502 of the tooth. In this example, a green intensity map 502g and a red intensity map 502r are used. Both the green intensity map 502g and the red intensity map 502r have background areas 504 (e.g. thick dentine and/or enamel). However, as previously discussed, in areas where the rigid material is thin the green intensity map 502g will show a thin region 506 corresponding to a thin part of the rigid material. The red intensity map 502r will not have the same thin region 506 as the red light is reflected from the dental pulp. Thus, the two intensity maps 502g and 502r can be subtracted (i.e. subtracting corresponding intensity values in the intensity maps) from one another to generate a subtracted map 508 which removes most of the intensity corresponding to the background areas 504 and clearly shows the thin region 506 where the dentine is relatively thin.

The thickness of the rigid material can be estimated based on the optical properties of the tooth. A first approach is to calibrate the system based on the assumption that optical properties of all teeth are similar. For example, the calibration may involve emitting light through a direction of the tooth which is known not to have pulp (and thus blood). The contrast of the thin region 506 where the pulp is seen in the green intensity map 502g may be an indication of the thickness of the dentine (and thus an indication of distance to the pulp).

Figure 6:
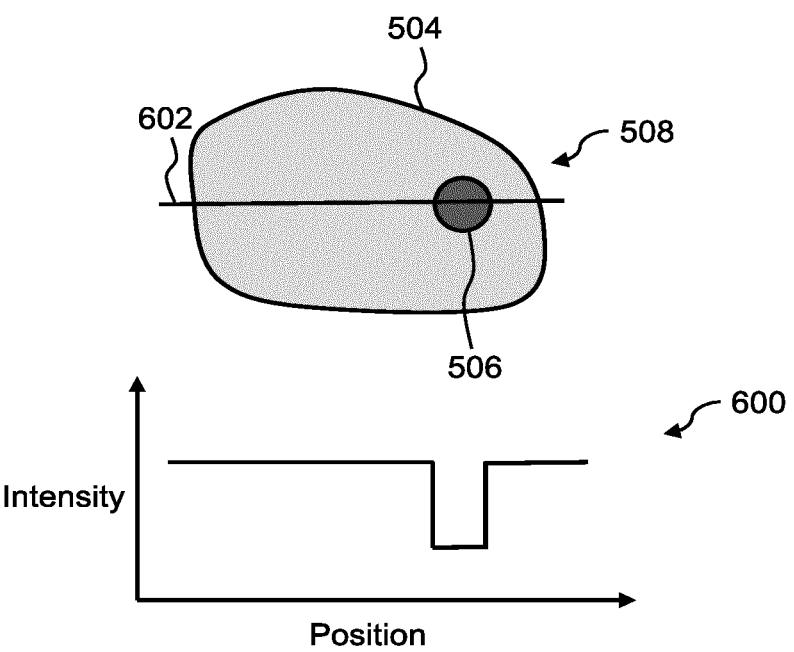
FIG. 6 shows the subtracted map of FIG. 5 and the intensity values along a line of the subtracted map.

FIG. 6 shows the subtracted map 508 of FIG. 5 and the intensity values along a line 602 of the subtracted map 508. The horizontal axis of the graph 600 represents a spatial dimension while the vertical axis represents the difference in intensity between the green intensity map 502g and the red intensity map 502r shown in FIG. 5. The graph 600 is shown for illustration purposes only.

It is possible to estimate the thickness of the rigid material from the difference between the two intensity maps shown in FIG. 5 (i.e. based on the subtracted map 508). The green intensity map 502g may be expressed as Ig(x,y) and the red intensity map 502r may be expressed as Ir(x,y). Thus, for a point (x1, y1), the thickness of the rigid material T may be expressed as: $T \sim (Ig(x1,y1)-Ir(x1,y1))/Ig(x1,y1)$. The term Ig(x1,y1)–Ir(x1,y1) corresponds to the subtracted map 508. In order to find a numerical thickness T, the probe may be calibrated prior to drilling.

This embodiment uses green light as the first wavelength and red light as the second wavelength. This is because these wavelengths are known to have different absorptivity values for blood and, additionally, green and red LEDs are standard and inexpensive. However, it will be appreciated by a person skilled in the art that any two wavelengths with different absorptivity values for blood will generate intensity maps which can be used in the same manner as explained above.

Figure 7:
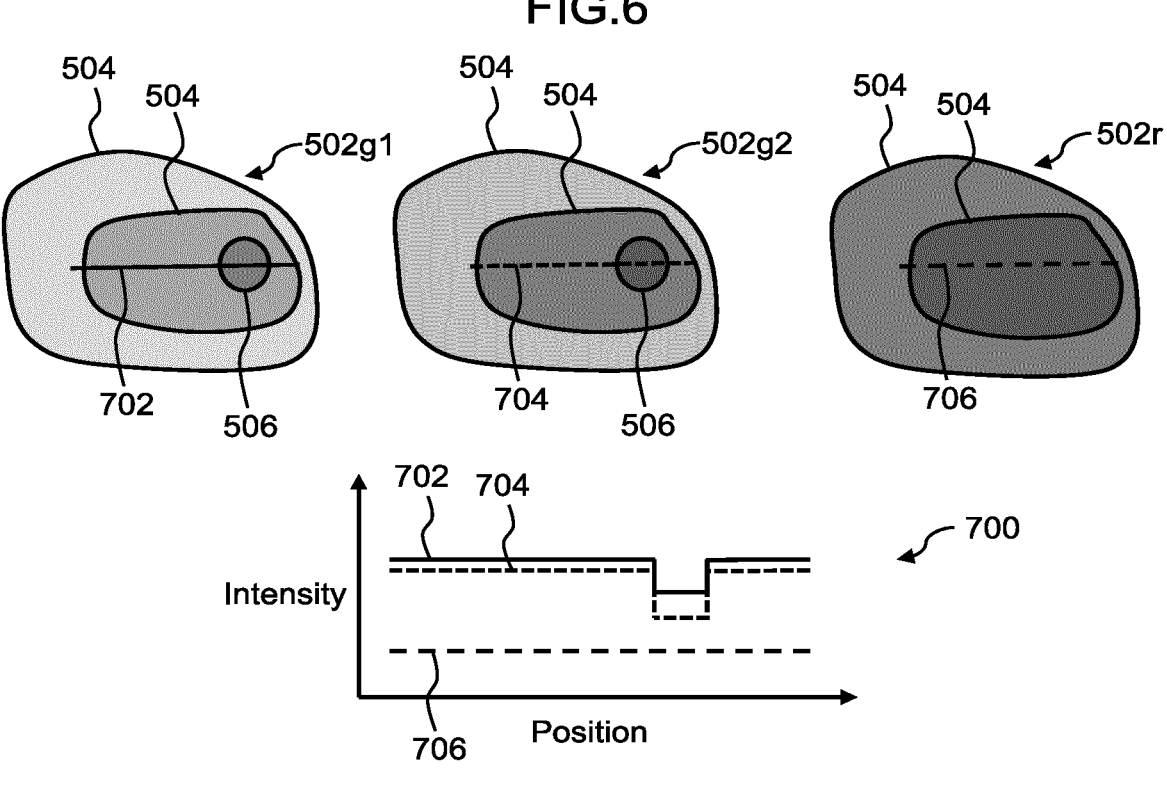
FIG. 7 shows a second embodiment according to the invention where triple color illumination is used to obtain intensity maps.

FIG. 7 shows a second embodiment according to the invention where triple color illumination is used to obtain intensity maps. In this embodiment, two green wavelengths and a single red wavelength are used to illuminate the tooth. For example, the tooth may be illuminated by light of a first green wavelength (e.g. 540 nm or 580 nm), a second green wavelength (e.g. 560 nm) and a red wavelength (e.g. 650 nm) and the corresponding intensity maps 502g1, 502g2 and 502r respectively are collected.

The background areas 504 in the intensity maps 502g1 and 502g2 are fairly similar. However, the contrast between the thin region 506 and the background areas 504 is different for both intensity maps 502g1 and 502g2. This can be seen in graph 700 where the intensity values across line 702 and 704 (corresponding to intensity maps 502g1 and 502g2 respectively) are shown. Similarly, the intensity values for the red intensity map 502r across line 706 are shown in graph 700. In this example, the intensity values from lines 702, 704 and 706 are only shown for the center-most section of the intensity maps for the sake of simplicity.

Triple color illumination can provide a more precise method of estimating the depth of the pulp as the ratio of the two green intensity maps is determined by the absorption constants of light in the blood, which is known. Additionally, blood peaks 201 and/or 202 (as shown in FIGS. 2 and 3B) could be identified by choosing two green wavelengths known to be at (or near) the peak and trough of a blood peak and determining the slope, in a spectral graph, between the intensities for the two green wavelengths.

In the case of triple color illumination with two green lights (at peak and trough of blood peak) and a red light, several thickness indications can be observed. For example, using lights of wavelengths 540 nm (g1), 560 nm (g2) and 650 nm (r):

Thickness of dentine>>2 mm—No blood peaks will be observable, the intensity of g2 will be higher than g1 and the intensity of r will be relatively high (see FIG. 3B).

Thickness of dentine between about 1-2 mm—Blood peaks will be observable, the intensity of g2 will be higher than g1 and the intensity of r will have a value lower than when the thickness of dentine is >>2 mm.

Thickness of dentine<<1 mm—No blood peaks will be observable, the intensity of g2 will be approximately equal to or lower than g1 and the intensity of r will be lower than when the thickness of dentine is between 1-2 mm.

Of course, it will be appreciated by a person skilled in the art that more detailed (and potentially numerical) indications of thickness could be obtained by observing the particular values of intensities for any of the three wavelengths, the ratio's between said intensities, the slope (in a spectral analysis) between the intensity values and/or the integral (in a spectral analysis) from g1 to r. In some cases, it may be necessary to calibrate the intensity values prior to, for example, drilling in order to estimate a numerical indication of thickness.

However, in some cases it may only be necessary to know whether the thickness of dentine is in the afore-mentioned ranges as, for example, the dentist can be told to stop drilling when the thickness falls in the range<<1 mm and may not need to know an exact thickness value.

The proposed detection of blood peaks could benefit further from multi-green light illumination (i.e. illumination with a plurality of green wavelengths), wherein the area of a triangle defined by the blood peaks could be calculated.

Dental Probe Device:

The above experimental discovery and methodology are explained in general terms in order to explain the discovery and theory behind the invention according to the claims. However, in practice, certain embodiments may not be practical as the device into which the invention will be integrated may need to physically fit into a subject's mouth thus limiting the size of the light source arrangement and the sensor arrangement. Additionally, the amount of processing required should not take too long as this would not be practicable during, for example, the drilling of a tooth.

Some existing dental probes already contain an illumination window and optical fibers to guide light to the tip of the probe to illuminate the area being drilled. Thus, it is further proposed to reuse existing illumination windows and optical fibers in existing probes and replace the white light illumination with multi-color illumination (preferably a green light, a red light and a white light).

As the illumination and the collection of light happens relatively far from the treatment location (i.e. the tip of the drill bit inserted into the probe) the spatial resolution would be lost if a single fiber optic is used to capture the reflected/ scattered light. Thus, it is proposed to collect the reflected light by a miniature optical camera integrated either behind or next to the illumination window. To avoid specular reflection, the optical camera may be equipped with a polarizer.

To increase the overall contrast of the images obtained by the camera, cross-polarizers may be used. Using cross-polarizers is a technique known to increase contrast in an optical image. The cross-polarizer solution avoids specular reflections from the illuminated area by utilizing orthogonal light polarization in transmission (light source) and reception (camera), thus increasing the contrast in the acquired image.

Figure 8:
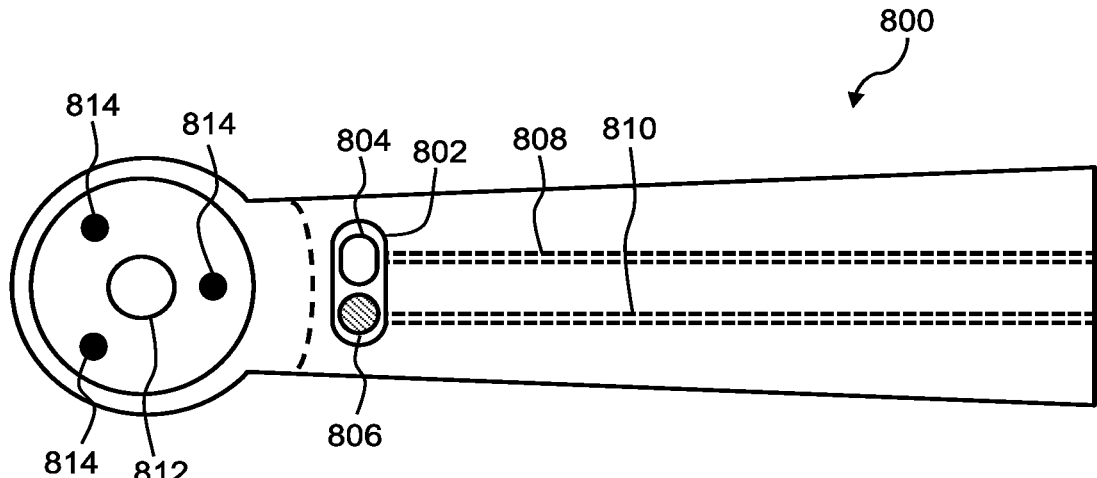
FIG. 8 shows an illustration of a probe with an illumination window.

FIG. 8 shows an illustration of a probe 800 with an illumination window 802. The illumination window 802 has an integrated multi-color light source arrangement 804 and a sensor arrangement 806 comprising a small camera. In this illustration, the probe 800 includes a rotor 812 for drilling functionality and three water outlets 814 at the distal end of the probe 800. However, it will be appreciated by a person skilled in the art that a probe 800 could be manufactured without the rotor 812 and/or the water outlets 814.

The light is brought to the illumination window 802 by a light guide 808 (which may be already present in some state-of-the-art probes) and connected to a multi-color light source, e.g. switchable LED's (not shown). The camera 806 is connected via a wire 810 to a processor (not shown) for processing the images (i.e. the intensity maps) taken by the camera 806, such that only minor modifications to the state-of-the-art probes are required.

In a different embodiment, the multi-color light source arrangement 804 and the camera 806 may be built into the probe 800 without the need of light guides 808 or the wire 810. For example, small LED's may be integrated directly behind the illumination window 802 and the existing channel for the light guide 808 could be used to host both power wires to the LED's and to the camera 806.

The probe can thus be used to evaluate, in real time, the presence and distance to the pulp through the dentine by determining the thickness of the dentine. It can give a warning to the doctor/dentist when a certain distance to the pulp is reached (e.g. >>2 mm, 1 mm, 0.2 mm, etc.).

In summary, the invention according to claim 1 is based on the experimental discovery that the presence of the blood inside the pulp leaves a unique footprint in the light reflected from the surface of the dental tissue. It is therefore proposed to include at least two narrow-band light sources, to illuminate the dental tissue, and an optical camera to collect the reflections into a dental probe. These reflections are then processed using the afore-mentioned methodology. Additionally, multi color illumination (e.g. triple color illumination) to improve the pulp detection sensitivity. The device can be used as stand-alone probe or integrated into a dental drill which makes it unobtrusive and simple to use.

The skilled person would be readily capable of developing a processor for carrying out any herein described method. Thus, each step of a flow chart may represent a different action performed by a processor, and may be performed by a respective module of the processor.

As discussed above, the system makes use of processor to perform the data processing. The processor can be implemented in numerous ways, with software and/or hardware, to perform the various functions required. The processor typically employs one or more microprocessors that may be programmed using software (e.g., microcode) to perform the required functions. The processor may be implemented as a combination of dedicated hardware to perform some functions and one or more programmed microprocessors and associated circuitry to perform other functions.

Examples of circuitry that may be employed in various embodiments of the present disclosure include, but are not limited to, conventional microprocessors, application specific integrated circuits (ASICs), and field-programmable gate arrays (FPGAs).

In various implementations, the processor may be associated with one or more storage media such as volatile and non-volatile computer memory such as RAM, PROM, EPROM, and EEPROM. The storage media may be encoded with one or more programs that, when executed on one or more processors and/or controllers, perform the required functions. Various storage media may be fixed within a processor or controller or may be transportable, such that the one or more programs stored thereon can be loaded into a processor.

Variations to the disclosed embodiments can be understood and effected by those skilled in the art in practicing the claimed invention, from a study of the drawings, the disclosure and the appended claims. In the claims, the word "comprising" does not exclude other elements or steps, and the indefinite article "a" or "an" does not exclude a plurality.

A single processor or other unit may fulfill the functions of several items recited in the claims.

The mere fact that certain measures are recited in mutually different dependent claims does not indicate that a combination of these measures cannot be used to advantage.

A computer program may be stored/distributed on a suitable medium, such as an optical storage medium or a solid-state medium supplied together with or as part of other hardware, but may also be distributed in other forms, such as via the Internet or other wired or wireless telecommunication systems.

If the term "adapted to" is used in the claims or description, it is noted the term "adapted to" is intended to be equivalent to the term "configured to".

Any reference signs in the claims should not be construed as limiting the scope.

The invention claimed is:

1. A device for estimating the thickness of rigid material in a tooth covering the pulp of the tooth, the device comprising:

a light source arrangement configured to emit light at a first wavelength and light at a second wavelength onto the tooth;

a sensor arrangement for measuring the intensity of light reflected and scattered from the tooth corresponding to the first and second wavelengths; and a processor configured to:

receive a first intensity map from the sensor arrangement corresponding to the first wavelength;

receive a second intensity map from the sensor arrangement corresponding to the second wavelength;

analyze the first intensity map and the second intensity map by determining an integral of intensity with respect to wavelength between the first wavelength and the second wavelength based on corresponding intensity values of the first intensity map and the second intensity map; and estimate a thickness value for the rigid material covering the pulp of the tooth by mapping the determined integral to a thickness value based on a predetermined relationship between said integral and thickness.

2. The device of claim 1, wherein blood has a higher absorptivity for light at the first wavelength than light at the second wavelength.

3. The device of claim 1, wherein the processor is configured to analyze the first intensity map and the second intensity map by determining the difference and/or a ratio between corresponding intensity values of the first intensity map and the second intensity map.

4. The device of claim 1, wherein the first wavelength is between 500 nm and 600 nm.

5. The device of claim 1, wherein the second wavelength is between 600 nm and 800 nm.

6. The device of claim 1, further comprising a cross-polarizer, wherein the cross-polarizer comprises a first polarizing element placed in front of the light source arrangement and a second polarizing element in front of the sensor arrangement and wherein the first polarizing element is orthogonal to the second polarizing element.

7. The device of claim 1, wherein the light source arrangement is further configured to emit light at a third wavelength and wherein:

blood has a higher absorptivity for light at the third wavelength than light at the second wavelength;

blood has a lower absorptivity for light at the third wavelength than light at the first wavelength;

the processor is further configured to receive a third intensity map from the sensor arrangement corresponding to the third wavelength; and the processor is further configured to analyze the third intensity map to assess the amount of light reflected and scattered from the tooth corresponding to the third wavelength.

8. The device of claim 1, wherein the light source arrangement comprises one or more light guides and one or more light emitting elements connected to a proximal end of the light guides.

9. The device of claim 1, wherein the first wavelength is between 530 nm and 550 nm.

10. The device of claim 1, wherein the first wavelength is between 570 nm and 590 nm.

11. A handheld dental probe comprising:

a housing comprising:

an illumination window at a distal end of the housing;

a rotor;

a light source arrangement configured to emit light at a first wavelength and light at a second wavelength onto the tooth;

a sensor arrangement for measuring the intensity of light reflected and scattered from the tooth corresponding to the first and second wavelengths; and a processor configured to:

receive a first intensity map from the sensor arrangement corresponding to the first wavelength;

receive a second intensity map from the sensor arrangement corresponding to the second wavelength;

analyze the first intensity map and the second intensity map by determining an integral of intensity with respect to wavelength between the first wavelength and the second wavelength based on corresponding intensity values of the first intensity map and the second intensity map; and estimate a thickness value for the rigid material covering the pulp of the tooth by mapping the determined integral to a thickness value based on a predetermined relationship between said integral and thickness, wherein the light source arrangement and the sensor arrangement are facing the illumination window.

12. The method of claim 11, wherein analyzing the first intensity map and the second intensity map comprises determining the difference and/or a ratio between corresponding intensity values of the first intensity map and the second intensity map.

13. A method for estimating the thickness of rigid material in a tooth covering the pulp of the tooth, the method comprising:

receiving a first intensity map from a sensor arrangement corresponding to a first wavelength, wherein the first intensity map comprises data of the intensity of light of the first wavelength reflected and scattered from the tooth;

receiving a second intensity map from the sensor arrangement corresponding to a second wavelength, wherein the second intensity map comprises data of the intensity of light of the second wavelength reflected and scattered from the tooth;

analyzing the first intensity map and the second intensity map by determining an integral of intensity with respect to wavelength between the first wavelength and the second wavelength based on corresponding intensity values of the first intensity map and the second intensity man; and estimating a thickness value for the rigid material covering the pulp of the tooth by mapping the determined integral to a thickness value based on a predetermined relationship between said integral and thickness.

14. The method of claim 13, wherein blood has a higher absorptivity for light at the first wavelength than light at the second wavelength.

* * * * *